(12) United States Patent
Heller et al.

(10) Patent No.: US 7,705,154 B2
(45) Date of Patent: *Apr. 27, 2010

(54) PROCESS FOR THE PREPARATION OF 2-SUBSTITUTED-5-(1-ALKYLTHIO) ALKYLPYRIDINES

(75) Inventors: Stephen T. Heller, Highland Park, NJ (US); Ronald Ross, Zionsville, IN (US); Nicholas M. Irvine, Westfield, IN (US); James M. Renga, Indianapolis, IN (US); Mark W. Zettler, Carmel, IN (US); Kim E. Arndt, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 324 days.

This patent is subject to a terminal disclaimer.

(21) Appl. No.: 11/704,759

(22) Filed: Feb. 9, 2007

(65) Prior Publication Data

US 2008/0132705 A1 Jun. 5, 2008

Related U.S. Application Data

(60) Provisional application No. 60/861,912, filed on Nov. 30, 2006.

(51) Int. Cl.
*C07D 213/12* (2006.01)
(52) U.S. Cl. .................................................... 546/250
(58) Field of Classification Search ................. 546/250, 546/251, 252
See application file for complete search history.

(56) References Cited

U.S. PATENT DOCUMENTS

2005/0228027 A1   10/2005   Zhu et al.

FOREIGN PATENT DOCUMENTS

WO   WO 2007095229 A2 *  8/2007
WO   PCT/US2007/003782      1/2009

OTHER PUBLICATIONS

U.S. Appl. No. 11/704,397, filed Feb. 9, 2007, Jim X. Huang, et al.
U.S. Appl. No. 11/704,756, filed Feb. 9, 2007, Kim E. Arndt, et al.
U.S. Appl. No. 11/704,796, filed Feb. 9, 2007, Kevin G. Meyer, et al.
U.S. Appl. No. 11/704,797, filed Feb. 9, 2007, Michael R. Loso, et al.
U.S. Appl. No. 11/704,820, filed Feb. 9, 2007, Yuanming Zhu, et al.
U.S. Appl. No. 11/704,824, filed Feb. 9, 2007, Jim X. Huang, et al.
U.S. Appl. No. 11/704,825, filed Feb. 9, 2007, James M. Renga, et al.
U.S. Appl. No. 11/704,842, filed Feb. 9, 2007, Michael R. Loso, et al.
U.S. Appl. No. 11/704,853, filed Feb. 9, 2007, Michael R. Loso, et al.
U.S. Appl. No. 11/705,185, filed Feb. 9, 2007, Michael R. Loso, et al.

* cited by examiner

*Primary Examiner*—Rita J Desai
*Assistant Examiner*—David K O'Dell
(74) *Attorney, Agent, or Firm*—Carl Corvin; Craig E. Mixan

(57) ABSTRACT

2-Substituted-5-(1-alkylthio)alkylpyridines are produced efficiently and in high yield by cyclization and thioalkylation.

6 Claims, No Drawings

PROCESS FOR THE PREPARATION OF 2-SUBSTITUTED-5-(1-ALKYLTHIO) ALKYLPYRIDINES

This application claims the benefit of U.S. Provisional Application Ser. No. 60/861,912 filed on Nov. 30, 2006.

BACKGROUND OF THE INVENTION

The present invention concerns processes for preparation of 2-substituted-5-(1-alkylthio)alkylpyridines.

The 2-substituted-5-(1-alkylthio)alkylpyridines are useful intermediates for the preparation of certain new insecticides; see, for example, U.S. Patent Publication 2005/0228027. It would be advantageous to produce 2-substituted-5-(1-alkylthio)alkylpyridines efficiently and in high yield.

SUMMARY OF THE INVENTION

One aspect of the present invention concerns a process for the preparation of 2-substituted-5-(1-alkylthio)alkylpyridine (I),

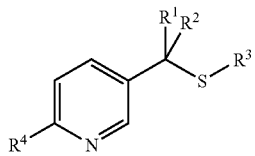

(I)

wherein
  $R^1$ and $R^2$ independently represent H, $C_1$-$C_4$ alkyl, or $R^1$ taken together with $R^2$ represent a 3- to 6-membered saturated ring optionally substituted with an O or a N atom; and
  $R^3$ represents $C_1$-$C_4$ alkyl; and
  $R^4$ represents $C_1$-$C_4$ alkyl or $C_1$-$C_4$ haloalkyl;

which comprises:

a) condensing a substituted enone (II)

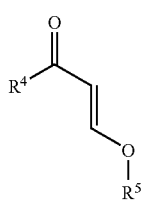

II wherein
  $R^4$ is as previously defined; and
  $R^5$ represents $C_1$-$C_4$ alkyl;

with an enamine (III)

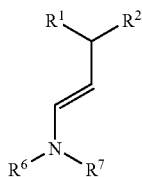

III wherein
  $R^1$ and $R^2$ are as previously defined; and
  $R^6$ and $R^7$ independently represent $C_1$-$C_4$ alkyl or $R^6$ and $R^7$ taken together with N represent a 5-membered saturated or unsaturated ring;

and cyclizing in the presence of ammonia or a reagent capable of generating ammonia to produce a 2,5-disubstituted pyridine (IV)

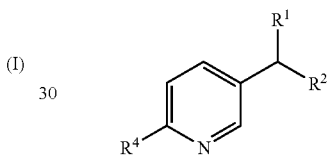

(IV)

wherein
  $R^1$, $R^2$ and $R^4$ are as previously defined;

b) chlorinating or brominating the 2,5-disubstituted pyridine (IV) to provide a haloalkylpyridine (V)

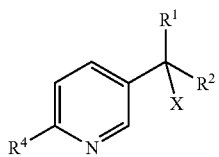

V wherein
  $R^1$, $R^2$ and $R^4$ are as previously defined; and
  X represents Cl or Br; and c) treating the haloalkylpyridine (V) with mercaptan salt (VI)

(VI)

wherein
  $R^3$ is as previously defined; and
  M represents an alkali metal to give 2-substituted-5-(1-alkylthio)alkylpyridine (I).

Yet another aspect of the present invention concerns a process for the preparation of 2-substituted-5-(1-alkylthio) alkylpyridine (I),

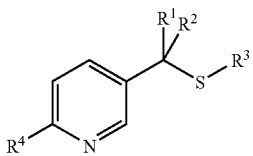

wherein
  $R^1$ and $R^2$ independently represent H, $C_1$-$C_4$ alkyl, or $R^1$ taken together with $R^2$ represent a 3- to 6-membered saturated ring optionally substituted with an O or a N atom; and
  $R^3$ represents $C_1$-$C_4$ alkyl; and
  $R^4$ represents $C_1$-$C_4$ alkyl or $C_1$-$C_4$ haloalkyl;

which comprises:

a) condensing a substituted enone (II)

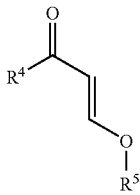

wherein
  $R^4$ is as previously defined; and
  $R^5$ represents $C_1$-$C_4$ alkyl;

with an enamine (III)

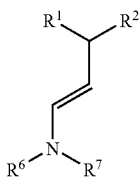

wherein
  $R^1$ and $R^2$ are as previously defined; and
  $R^6$ and $R^7$ independently represent $C_1$-$C_4$ alkyl or $R^6$ and $R^7$ taken together with N represent a 5-membered saturated or unsaturated ring;

and cyclizing in the presence of ammonia or a reagent capable of generating ammonia to produce a 2,5-disubstituted pyridine (IV)

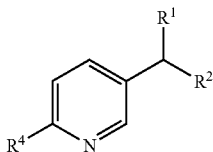

wherein
  $R^1$, $R^2$ and $R^4$ are as previously defined; and b) treating the 2,5-disubstituted pyridine (IV) with dialkyl disulfide (VII) and strong base, $$R^3SSR^3 \quad\quad (VII)$$

wherein
  $R^3$ is as previously defined;

to give 2-substituted-5-(1-alkylthio)alkylpyridine (I).

Another aspect of the invention is the novel compounds having the formula (IV)

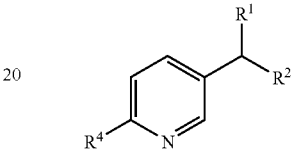

wherein
  $R^1$ and $R^2$ independently represent H, $C_1$-$C_4$ alkyl, or $R^1$ taken together with $R^2$ represent a 3- to 6-membered saturated ring optionally substituted with an O or a N atom; and
  $R^4$ represents $C_1$-$C_4$ haloalkyl.

Another aspect of the invention is the novel compounds having the formula (V)

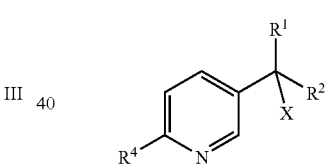

wherein
  $R^1$ and $R^2$ independently represent H, $C_1$-$C_4$ alkyl, or $R^1$ taken together with $R^2$ represent a 3- to 6-membered saturated ring optionally substituted with an O or a N atom;
  $R^4$ represents $C_1$-$C_4$ haloalkyl; and
  X represents Cl or Br.

DETAILED DESCRIPTION OF THE INVENTION

Unless specifically limited otherwise, the term "alkyl" (including derivative terms such as "haloalkyl"), as used herein, include straight chain, branched chain, and cyclic groups. Thus, typical alkyl groups are methyl, ethyl, 1-methylethyl, propyl, 1,1-dimethylethyl, and cyclopropyl. The term "halogen" includes fluorine, chlorine, bromine and iodine. The term "haloalkyl" includes alkyl groups substituted with from one to the maximum possible number of halogen atoms.

One aspect of the present invention concerns a process for the preparation of 2-substituted-5-(1-alkylthio)alkylpyridine (I),

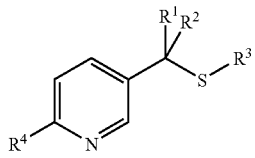

(I)

wherein
  $R^1$ and $R^2$ independently represent H, $C_1$-$C_4$ alkyl, or $R^1$ taken together with $R^2$ represent a 3- to 6-membered saturated ring optionally substituted with an O or a N atom; and
  $R^3$ represents $C_1$-$C_4$ alkyl; and
  $R^4$ represents $C_1$-$C_4$ alkyl or $C_1$-$C_4$ haloalkyl;

which comprises:

a) condensing a substituted enone (II)

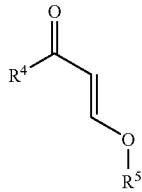

II wherein
  $R^4$ is as previously defined; and
  $R^5$ represents $C_1$-$C_4$ alkyl;

with an enamine (II)

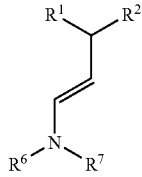

III wherein
  $R^1$ and $R^2$ are as previously defined; and
  $R^6$ and $R^7$ independently represent $C_1$-$C_4$ alkyl or $R^6$ and $R^7$ taken together with N represent a 5-membered saturated or unsaturated ring;

and cyclizing in the presence of ammonia or a reagent capable of generating ammonia to produce a 2,5-disubstituted pyridine (IV)

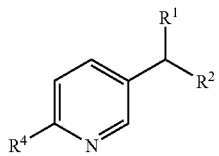

(IV)

wherein
  $R^1$, $R^2$ and $R^4$ are as previously defined;

b) chlorinating or brominating the 2,5-disubstituted pyridine (IV) to provide a haloalkylpyridine (V)

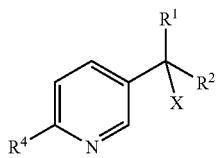

V wherein
  $R^1$, $R^2$ and $R^4$ are as previously defined; and
  X represents Cl or Br; and c) treating the haloalkylpyridine (V) with mercaptan salt (VI)

$$R^3S^-M^+ \qquad (VI)$$

wherein
  $R^3$ is as previously defined; and
  M represents an alkali metal to give 2-substituted-5-(1-alkylthio)alkylpyridine (I).

α,β-Unsaturated ketones (II) starting materials are commercially available or can be prepared from the corresponding vinylogous substrates and acylating agents. Typically, alkylvinyl ethers can be acylated with haloalkylacetic anhydrides to yield compounds of type (II). Enamines (III) starting materials can be conveniently prepared from the addition of a suitably substituted amine to the appropriately substituted aldehyde in the presence of a water adsorbing material, with or without a suitable solvent. Typically, the appropriate substituted propionaldehyde is reacted with an anhydrous disubstituted amine at about −20° C. to about 20° C. in the presence of a desiccant such as anhydrous potassium carbonate, and the product is isolated by distillation.

In step a), approximately equimolar quantities of the α,β-unsaturated ketone (II) and the enamine (III) and ammonia are required in the process, although 2-4 fold excesses of the ammonia or the ammonia precursor are often preferred.

Typical reagents capable of generating ammonia include, for example, 1) an ammonium salt of an acid, preferably an organic acid, 2) formamide, or 3) formamide with an acid or acid salt. The ammonium salt of any aliphatic or aromatic organic acid can be used, but for convenience of processing, the ammonium salts of $C_1$-$C_4$ alkanoic acids are preferred. Ammonium formate and ammonium acetate are most preferred.

Step a) is preferably conducted in a polar high-boiling solvent that is miscible with water. Preferred solvents include amides such as formamide, dimethyl formamide, dimethyl acetamide, alcohols such as methanol, ethanol, isopropanol, (2-methoxy)ethanol and alkylnitriles, with acetonitrile being particularly preferred.

The reaction is conducted at a temperature from about −20° C. to about 150° C. Temperatures from about 0° C. to about 80° C. are usually preferred.

The product is isolated by conventional techniques such as silica gel chromatography or fractional distillation.

In a typical reaction, the α,β-unsaturated ketone (II) and enamine (III) are dissolved in the polar solvent at about −5° C. to about 20° C. and agitated until the α,β-unsaturated ketone (II) and enamine (III) are consumed. The ammonium salt of the organic acid is then added, and the mixture is heated until the reaction is complete. After dissolving in a non water miscible solvent and washing with water and, optionally, brine, the 2,5-disubstituted pyridine (IV) is isolated by silica gel column chromatography, or preferably vacuum distillation .

In step b), 2,5-disubstituted pyridine (IV) is selectively halogenated with N-chlorosuccinimide, or preferably N-bromosuccinimide at about −78° C. to about 100° C. in a suitable solvent such as methylene chloride and optionally a catalytic amount of a Lewis acid such as zirconium tetrachloride or free radical initiator such as benzoyl peroxide. The resulting 2-substituted-5-monohaloalkyl pyridine (V) is then further reacted in step c) with a mercaptan salt (VI)) in a suitable solvent such as ethanol or tetrahydrofuran at temperatures between about 0° C. and about 60° C. to obtain 2-substituted-5-(1-alkylthio)alkylpyridine (I)

Alternatively, the 2,5-disubstituted pyridine (IV) from step a), is reacted with dialkyl disulfide (VII) and strong base, such as lithium diisopropylamide in a suitable solvent such as tetrahydrofuran or diethyl ether to give 2-substituted-5-(1-alkylthio)pyridine (I).

Typically, the 2,5-disubstituted pyridine (IV) is treated with a strong base such as lithium diisopropylamide in a suitable solvent such as tetrahydrofuran at about −100° C. to about 0° C. and subsequently treated with dialkyl disulfide (VII) to give 2-substituted-5-(1-alkylthio)alkylpyridine (I) which can be isolated by conventional methods such as silica gel chromatography or vacuum distillation.

The following examples are presented to illustrate the invention.

EXAMPLES

Example 1

Preparation of 5-(1-Methylthioethyl)-2-trifluoromethylpyridine

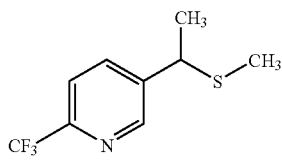

Step 1. Preparation of 1-But-1-enylpyrrolidine

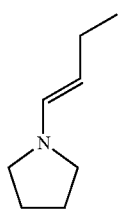

To a dry 500 milliliter (mL) three neck round bottom flask equipped with magnetic stirrer, nitrogen inlet, addition funnel, and thermometer, was charged with pyrrolidine (83.45 mL, 1.0 mmol) and potassium carbonate (34.55 g, 0.25 mol). The mixture was cooled to 0° C. and butanal (30.05 grams (g), 0.42 mol) was added dropwise with stirring under nitrogen at ad rate that maintained the temperature below 15° C. After the addition was complete (~10 minutes), the cooling bath was taken away and the reaction mixture allowed to warm to room temperature over three hours. The reaction mixture was filtered through a scintered glass filter to remove the solids. The solid was washed thoroughly with ether, and combined with the filtrate, which was concentrated on the rotary evaporator to give the crude 1-but-1-enylpyrrolidine which was purified by vacuum distillation @15 mmHg 65-78° C.; $^1$H NMR (CDCl$_3$): δ 6.20 (d, 1H), 4.18 (q, 1H), 2.95 (m, 4H), 1.80, (m, 4H), 0.97 (d, 3H).

Step 2. Preparation of 5-Ethyl-2-trifluoromethylpyridine

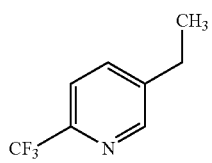

To a dry 500 mL round bottom flask equipped with magnetic stirrer, nitrogen inlet, addition funnel, thermometer, and reflux condenser was charged 1-but-1-enylpyrrolidine but-1-enylpyrrolidine (15.0 mL, 0.12 mol, freshly distilled @15 mmHg 65-78° C.) and anhydrous acetonitrile (150 mL). 4-Ethoxy-1,1,1-trifluorobut-3-en-2-one (24 mL, 0.12 mol) was added dropwise and stirred at room temperature for two hours. Ammonium acetate (18.5 g, 0.389 mol) was then added in one portion, and the mixture heated to reflux for one hour and then at ambient temperature overnight. The reaction mixture was poured into water (200 mL) and the aqueous mixture was extracted with ethyl acetate (3×50 mL). The combined organic layers were washed with water, brine and dried (MgSO4), filtered, and concentrated under reduced pressure on a rotary evaporator. The residue was purified by column chromatography on silica gel with a gradient (15 min) of 100% hexane to 50% ethyl acetate, 50% hexane. The pure fractions were combined, and concentrated in vacuo to afford 12.6 g of 5-ethyl-2-trifluoromethylpyridine as a red liquid; $^1$H NMR (CDCl$_3$) δ 8.58 (s, 1H), 7.68 (d, 1H), 7.61 (d, 1H), 2.73 (q, 1H), 1.28 (d 3H).

Step 3. Preparation of 5-(1-Bromoethyl)-2-trifluoromethylpyridine

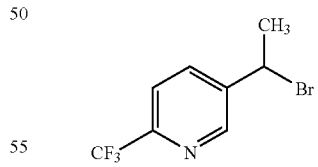

N-Bromosuccinimide (1.78 g, 0.01 mol) was added to anhydrous fresh methylene chloride (60 mL) at room temperature under an atmosphere of nitrogen. Once dissolved, the solution was cooled to 0° C. The 5-ethyl-2-trifluoromethyl-pyridine pyridine (1.75 g, 0.01 mol) was dissolved in a small amount of anhydrous methylene chloride and was added via syringe followed by zirconium tetrachloride (117 mg, 0.5 mmol). The ice bath was taken away and the mixture allowed to stir at room temperature overnight. TLC showed complete reaction (9:1, hexane:EtOAc). The reaction mixture was quenched with saturated sodium bicarbonate (25 mL). The organic layer was separated and washed with brine and dried (MgSO$_4$). The residue was purified by column chromatography (1:20, EtOAc:Hex) to give the product, 2.04 g (80%), as a pale yellow liquid; $^1$H NMR (CDCl$_3$) δ 8.77 (s, 1H), 7.97 (d, 1H), 7.69 (d, 1H), 5.21 (q, 1H), 2.08 (d, 3H).

Step 4. Preparation of
5-(1-Methylthioethyl)-2-trifluoromethylpyridine

A solution of 5-(1-bromoethyl)-2-trifluoromethylpyridine (1.02 g, 4.0 mmol) in ethanol (30 mL) was cooled to 0° C. under an atmosphere of nitrogen. Sodium methyl mercaptide (364 mg, 5.2 mmol) was added batchwise. Once added, the ice bath was removed and the reaction stirred at room temperature under nitrogen overnight. TLC (9:1, hexane:EtOAc) showed complete reaction. The turbid solution was quenched with water and extracted with ether. The organic layer was then washed with brine and dried (MgSO$_4$). The solvent was removed in vacuo to provide the crude product as a pale yellow liquid, 0.83 g (93%); $^1$H NMR (CDCl$_3$) δ 8.65 (s, 1H), 7.89 (d, 1H), 7.67 (d, 1H), 3.93 (q, 1H), 1.94 (s, 3H), 1.62 (d, 3H).

What is claimed is:

1. A process for the preparation of 2-substituted-5-(1-alkylthio)alkylpyridine (I), wherein
R$^1$ and R$^2$ independently represent H, or C$_1$-C$_4$ alkyl; and
R$^3$ represents C$_1$-C$_4$ alkyl; and
R$^4$ represents C$_1$-C$_4$ alkyl or C$_1$-C$_4$ haloalkyl;
which comprises:
a) condensing a substituted enone (II)

wherein
R$^4$ is as previously defined; and
R$^5$ represents C$_1$-C$_4$ alkyl;

with an enamine (III)

wherein
R$^1$ and R$^2$ are as previously defined; and
R$^6$ and R$^7$ independently represent C$_1$-C$_4$ alkyl or R$^6$ and R$^7$ taken together with N represent a 5-membered saturated ring; and
cyclizing in the presence of ammonia or a reagent capable of generating ammonia to produce a 2,5-disubstituted pyridine (IV)

wherein R$^1$, R$^2$ and R$^4$ are as previously defined;
b) chlorinating or brominating the 2,5-disubstituted pyridine (IV) to provide a haloalkylpyridine (V)

wherein
R$^1$, R$^2$ and R$^4$ are as previously defined; and
X represents Cl or Br; and
c) treating the haloalkylpyridine (V) with mercaptan salt (VI)

$$R^3S^-M^+ \quad (VI)$$

wherein
R$^3$ as previously defined; and
M represents an alkali metal
to give 2-substituted-5-(1-alkylthio)alkylpyridine (I).

2. The process of claim 1 in which R$^4$ represents CF$_3$.

3. The process of claim 2 in which R$^1$ represents H, R$^2$ represents CH$_3$, and R$^3$ represents CH$_3$.

4. A process for the preparation of 2-substituted-5-(1-alkylthio)alkylpyridine (I),

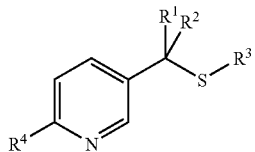

(I)

wherein
$R^1$ and $R^2$ independently represent H, $C_1$-$C_4$ alkyl, or $R^1$ taken together with represent a 3- to 6-membered saturated ring optionally substituted with an O or a N atom; and
$R^3$ represents $C_1$-$C_4$ alkyl; and
$R^4$ represents $C_1$-$C_4$ alkyl or $C_1$-$C_4$ haloalkyl;
which comprises:
a) condensing a substituted enone (II)

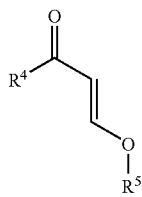

II wherein
$R^4$ is as previously defined; and
$R^5$ represents $C_1$-$C_4$ alkyl;

with an enamine (III)

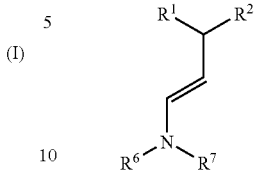

III wherein
$R^1$ and $R^2$ are as previously defined; and
$R^6$ and $R^7$ independently represent $C_1$-$C_4$ alkyl or $R^6$ and $R^7$ taken together with N represent a 5-membered saturated or unsaturated ring; and cyclizing in the presence of ammonia or a reagent capable of generating ammonia to produce a 2,5-disubstituted pyridine (IV)

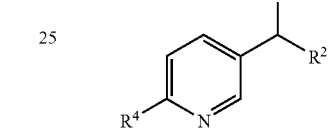

(IV)

wherein
$R^1$, $R^2$ and $R^4$ are as previously defined; and
b) treating the 2,5-disubstituted pyridine (IV) with dialkyl disulfide (VII) and strong base,

  $R^3SSR^3$ (VII)

wherein
$R^3$ as previously defined;
to give 2-substituted-5-(1-alkylthio)alkylpyridine (I).

5. The process of claim 4 in which $R^4$ represents $CF_3$.

6. The process of claim 5 in which $R^1$ represents H, $R^2$ represents $CH_3$, and $R^3$ represents $CH_3$.

* * * * *